United States Patent [19]
Nelson

[11] Patent Number: 5,231,991
[45] Date of Patent: Aug. 3, 1993

[54] APPARATUS FOR PROMOTING WASTE-FREE PRIMARY FLOW IN A PATIENT MONITORING DEVICE

[75] Inventor: Craig H. Nelson, Hillsboro, Oreg.

[73] Assignee: Protocol Systems, Inc., Beaverton, Oreg.

[21] Appl. No.: 633,244

[22] Filed: Dec. 21, 1990

[51] Int. Cl.[5] .............................................. B01D 53/24
[52] U.S. Cl. ..................... 128/716; 128/719; 128/204.14; 128/205.27; 55/158; 73/19.12
[58] Field of Search ............ 128/716, 718, 719, 204.14, 128/205.27; 55/158, 159, 164; 73/19; 210/435

[56] References Cited
U.S. PATENT DOCUMENTS

| | | | |
|---|---|---|---|
| 4,366,700 | 1/1983 | Bouck | 73/19 |
| 4,516,580 | 5/1985 | Polanyi | 128/632 |
| 4,549,553 | 10/1985 | Hochberg | 128/719 |
| 4,695,382 | 9/1987 | Cronin | 210/436 |
| 4,729,773 | 3/1988 | Shirato et al. | 55/158 |
| 4,764,346 | 8/1988 | Lewis et al. | 128/205.12 |
| 4,924,860 | 5/1990 | Larsen et al. | 128/719 |
| 4,997,463 | 3/1991 | Ricciardelli | 128/719 |

Primary Examiner—Kyle L. Howell
Assistant Examiner—George Manuel
Attorney, Agent, or Firm—Kolisch, Hartwell, Dickinson, McCormack & Heuser

[57] ABSTRACT

Apparatus for promoting waste-free primary flow in a patient monitoring device is disclosed and includes a waste trap with a body defining a waste chamber with the body including an entry port for communication with a primary channel of the device, and an exit port for communication with a secondary channel of the device. The exit port has a first cross-sectional area. The exit port is defined by a porous, gas-permeable, waste-blocking member that extends into the chamber to promote waste-free primary flow in any orientation of the trap. The member has a total-pore area exceeding the first cross-sectional area. Operatively connected between the ports is means for monitoring the differential pressure therebetween and for sending signals representative of such pressure to associated control circuitry of the device for determining the volume of waste in said body based on signals received from the monitoring means.

3 Claims, 2 Drawing Sheets

APPARATUS FOR PROMOTING WASTE-FREE PRIMARY FLOW IN A PATIENT MONITORING DEVICE

BACKGROUND OF THE INVENTION

The present invention relates to waste traps for patient monitoring devices such as capnometers, and more particularly to apparatus for promoting waste-free primary flow in such waste traps as well as such devices in general.

Certain patient monitoring devices include gas/waste separators for separating a desired, to-be-analyzed gas mixture from waste material such as sputum and spittle. One such device that includes a separator is a capnometer. Capnometers are used to measure the percentage of $CO_2$ in a patient's breath. Examples of such capnometers and separators are disclosed in U.S. Pat. No. 4,579,568 to Ricciardelli and Blazel, U.S. Pat. No. 4,592,368 to Ricciardelli and Sommer, and U.S. Pat. No. 4,713,095 to Ricciardelli, each of which is incorporated herein by reference.

As is known to those skilled in the art and as described in the above patents, conventional capnometers are designed with a channel that conducts a patient's breath sample from a mouthpiece to a gas/waste separator. Coupled to the separator are two channels for conducting gas/waste.

One such channel is called the primary, or gas-sensing channel and the other, the secondary channel. The channels may be designed so that either a single pump or dual pumps maintain negative pressure in both channels. If a single-pump design is used the secondary channel is called the blow-down channel. As used herein, secondary channel means the non-gas-sensing channel of a capnometer whether or not such channel is a blow-down channel or a secondary channel.

The gas-sensing channel is designed to conduct a relatively high percentage of the patient's breath, referred to herein as the gas-sensing or primary flow, from the separator to a gas-sampling chamber. The gas-sampling chamber will be referred to herein as an optical bench, or bench.

The secondary channel is designed to conduct a relatively small percentage of the patient's breath from the separator through a waste trap, and through a pump where it exits the capnometer.

Conventional separators such as those described in the above patents include three ports. A first port is for receiving a patient sample conducted from the patient airway; a second port is for allowing gas to be conducted to the optical bench; a third port is for allowing waste to be conducted to the waste trap.

Secondary flow begins where gas, and waste, flow from the separator into the waste trap through a suitable port. Then, as long as nothing obstructs secondary flow, gas flows through and out of the trap via a suitable port while waste remains in the trap.

As described and exemplified in the above patents, several proposals have been made concerning improvements to the separator in conventional capnometers.

However, until now, no one has proposed apparatus for promoting waste-free primary flow during a measurement cycle before the waste trap becomes full.

As is known to those skilled in the art, secondary flow is necessary to ensure that proper gas/waste separation will take place in the separator. Proper separation is extremely important because, in its absence, waste will enter and contaminate the primary channel including the optical bench, thus ruining the desired gas measurement. In addition, substantial cost will be incurred by having to dismantle the capnometer to clean contaminated components.

Conventional capnometer waste traps do not promote waste-free primary flow for several reasons. First, traps such as those disclosed in U.S. Pat. No. 4,579,568 to Ricciardelli and Blazel, U.S. Pat. No. 4,592,368 to Ricciardelli and Sommer cannot operate in all orientations. That is, the traps disclosed therein allow undesired waste flow into the secondary channel from the trap if they are tilted or inverted during use.

Likewise, U.S. Pat. No. 4,886,528 to Aaltonen et al. discloses a trap with a water separator positioned in a secondary channel downstream of the trap, but such apparatus is not operable in all orientations. That is, the trap will allow undesired waste flow into the water separator if the trap is tilted/inverted during use. Such waste flow may block gas-flow through the separator, thus blocking secondary flow.

It is undesirable to allow waste in the secondary channel because it could foul the pump or tubing. Even worse, waste could block secondary flow causing improper or faulty gas/waste separation in the separator. Improper/faulty gas/waste separation results in waste entering the primary flow which ruins desired gas measurement and contaminates the optical bench.

It is therefore an object of the present invention to provide apparatus for promoting waste-free primary flow in a patient monitoring device during a measurement cycle.

A further object of the present invention is to provide apparatus for preserving secondary flow in a patient monitoring device during a measurement cycle.

Another object of the present invention is to provide a waste trap for conventional patient-monitoring devices that preserves secondary flow independent of the orientation of the trap.

Yet another object of the present invention is to provide means for monitoring the volume of waste in the trap during the measurement cycle and for sending signals to conventional control circuitry that is designed to activate associated conventional audible/visible alarm devices upon receiving a threshold signal. Such monitoring/sending means would thus promote waste-free primary flow and preserve secondary flow by letting the user know when the trap is nearly full and ready to be emptied.

SUMMARY OF THE INVENTION

The present invention overcomes the drawbacks of conventional waste-traps for patient-monitoring-devices by providing apparatus for promoting waste-free primary flow in a patient monitoring device during a measurement cycle. The apparatus forms part of such a device and includes a waste trap with a body defining a waste chamber. The body includes an entry port for communication with the gas-sensing channel, and an exit port for communication with the secondary channel. The exit port has a first cross-sectional area.

Secondary flow is directed through the body from the entry port to the exit port where it continues through the secondary channel. A porous, gas-permeable, waste-blocking member defines the exit port and extends into the chamber. The member has a total-pore area exceeding the first cross-sectional area, for promoting waste-free primary flow independent of the orientation of the body.

The apparatus of the present invention may also include means, operatively connected between the ports, for monitoring the differential pressure in the channels. Such monitoring means is also operable to send signals representative of such pressure to control circuitry of the device for determining the volume of waste in the body based on signals received from the monitoring means.

These and additional objects and advantages of the present invention will be more readily understood after a consideration of the drawings and the detailed description of the preferred embodiment.

DETAILED DESCRIPTION OF THE PREFERRED EMBODIMENT

Figure 1:
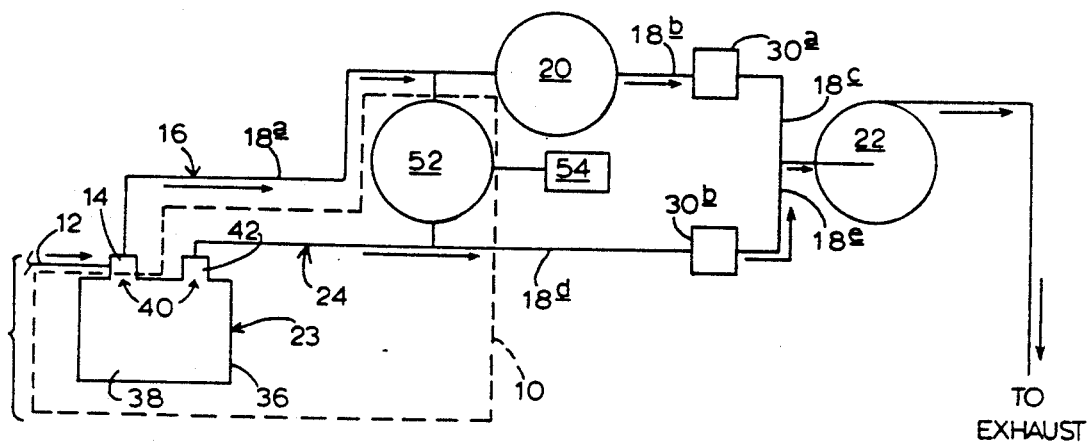
FIG. 1 is a schematic block diagram showing the apparatus of the present invention forming part of a conventional capnometer.

Referring now to the drawings, FIG. 1 shows the apparatus of the present invention at 10 forming part of a capnometer. Preliminarily, it should be understood that the capnometer to which apparatus 10 is connected may include electronic control circuitry (undepicted) as known to those skilled in the art. An example of capnometer components that are usable with apparatus 10 is that identified by model no. 9000 from Acumed Technologies, Inc. of Brookfield, Wis. ("Acumed").

Also, the capnometer is but one example of a patient monitoring device that may be usable with apparatus 10. That is, as will be understood, apparatus 10 may form part of any patient monitoring device that conducts patient breath in primary and secondary channels.

Again directing the reader's attention to FIG. 1, the various capnometer components that are usable with apparatus 10 will now be described. A suitable patient-breath-delivery tube 12 conducts patient breath (undepicted) from a patient (undepicted) to a conventional gas/liquid separator 14. Separator 14 may be formed like the separator chamber described in U.S. Pat. No. 4,579,568 or the separator described in U.S. Pat. No. 4,713,095.

From separator 14, fluid flow is divided into two channels. Referring to the top of separator 14 in FIG. 1, a primary, or gas-sensing channel 16 conducts a relatively large percentage of the gas component of patient breath via suitable sensor-tubing 18a to a conventional optical bench 20 for % $CO_2$-determination.

The phrase primary flow is used herein to refer to the flow of gas in channel 16 and is shown by appropriate arrows in FIG. 1. From bench 20, primary flow continues through tubing 18b to a pump 22 where it is conducted to exhaust via tubing 18c. Pump 22 may be any suitable pump such as a diaphragm pump. Primary flow occurs because pump 22 produces a desired negative pressure in channel 16.

Referring to the bottom of separator 14 in FIG. 1, secondary flow proceeds through a waste trap 23 and into a secondary channel 24 which conducts it to pump 22 via tubing 18d–e. In the capnometer design shown in FIG. 1, channel 24 is what is known as a blow-down channel because it reconnects to primary channel 16 before both channels are connected to single pump 22.

Those skilled in the art know that an alternative capnometer design may include structuring channel 24 so that it does not reconnect to channel 16. Such a design would require a second pump (undepicted) for connecting to channel 24.

Also, those skilled in the art know that the capnometer in FIG. 1 may include a purge mechanism with a purge pump (undepicted) and a suitable vent mechanism(s) but such mechanisms are not depicted because they form no part of the present invention.

Concerning material choice for the tubing, preferably sensor tubing 18a and tubing 18b–e are made of silicon rubber and are suitable for withstanding the negative pressure associated with conventional capnometers. Special considerations are required for sensor tubing 18a because there must be a proper balance between the seemingly opposite requirements of low-flow resistance and minimum-volume capacity. Tubing with low-flow resistance is necessary to ensure proper flow of gas to the bench and minimum-volume capacity is necessary to prevent substantial mixing of $CO_2$ and air in the tubing. Those skilled in the art know that such $CO_2$/air mixing occurs according to known laminar flow principles.

With the above special considerations in mind, it is preferable that sensor tubing 18a be made of suitable plastic tubing with an inside diameter of approximately 0.040-inches. The choice of material for tubing 18b–e does not involve such special considerations and may take the form of any suitable tubing.

Continuing with the description of capnometer design considerations, those skilled in the art know that capnometers can be structured to conduct desired percentages of the gas component of patient breath via the gas-sensing channel and the secondary channel. Key design considerations include the pump flow-rate setting, the length and inside diameter of the tubing, and the number and type of so-called flow resistors operatively connected to the tubing of the capnometer.

Preferably, apparatus 10 should be used with a capnometer that conducts approximately 92.5% (by volume) of the gas component of the patient's breath via the gas-sensing channel and approximately 7.5% (by volume) of the gas component via the secondary channel when waste trap 23 is empty. Such a difference in gas flow through channels 16 and 24 is known as a blow-down ratio.

Referring again to FIG. 1, those skilled in the art know to obtain the desired blow-down ratio by connecting suitable flow resistors 30a, 30b to channel 16 and channel 24, respectively, and by choosing a suitable pump.

The flow resistors may take the form of any known flow resistor. A suitable type of flow resistor is one formed of a desired length of tubing that is suitably wound to form a coil and includes a desired inside diameter for controlling fluid flow.

Still referring to FIG. 1, pump 22 is set to draw approximately 85-ml/min. through the capnometer. With resistors 30a, 30b connected to channels 16 and 24, respectively, primary flow is approximately 80-ml/min. and secondary flow is approximately 5-ml/min. For proper operation of apparatus 10, secondary flow must be ˆ 1-ml/min.

Figure 2:
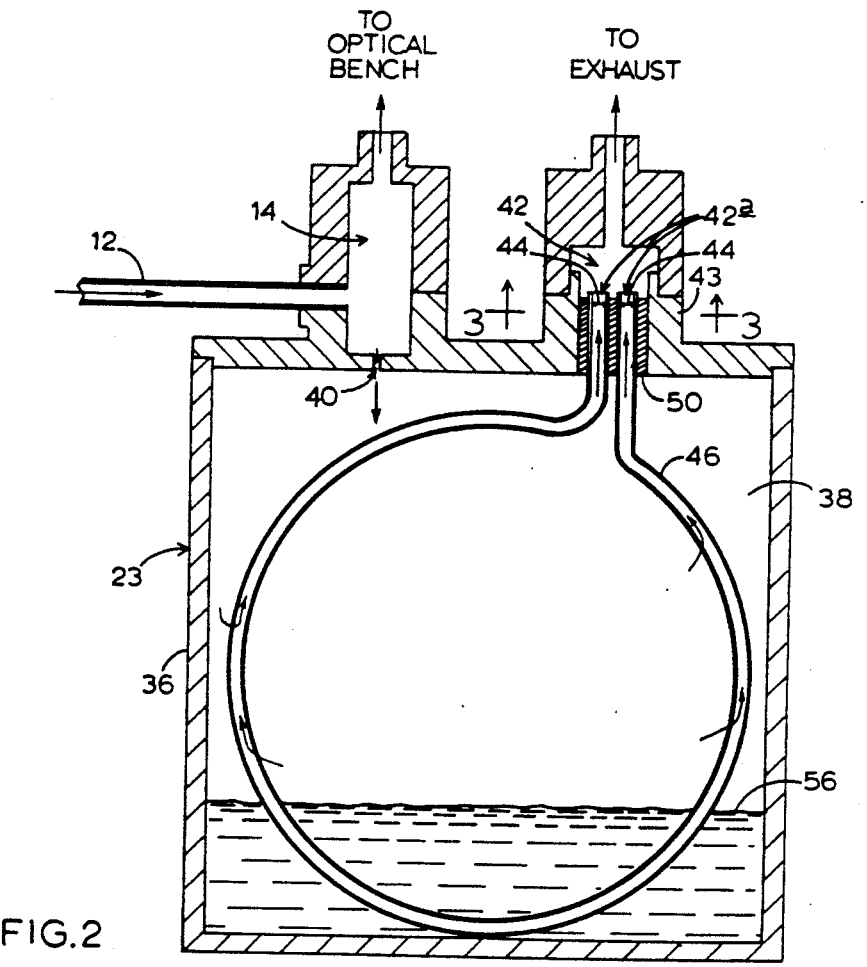
FIG. 2 is a fragmentary, sectional view of the portion of the apparatus shown generally adjacent the bracket in FIG. 1, showing on a larger scale, that portion of the apparatus of FIG. 1 that is disposable, with an associated conventional gas/liquid separator, the latter shown by block diagram.
Figure 3:
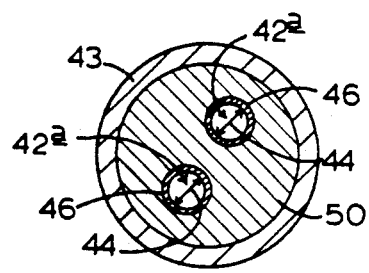
FIG. 3 is a sectional view through line 3—3 of FIG. 2, on a slightly larger scale.
Figure 4:
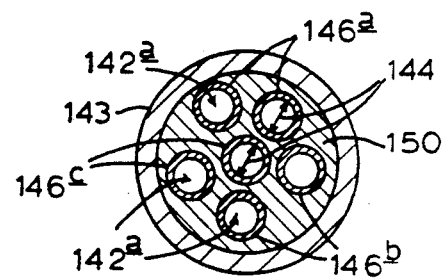
FIG. 4 is like FIG. 3 except it shows a second embodiment of the invention.

Referring ahead to FIGS. 2–4, details of trap 23 will now be described. Preliminarily, it should be noted that trap 23, including the below-described components, is disposable. Referring to FIGS. 1 and 2, trap 23 includes a body 36 defining a waste chamber 38. Body 36 includes an entry port 40, which may have an inside diameter of approximately 0.020 in., for communication with gas-sensing channel 16 and an opening 42 for communication with secondary channel 24 via exit port 42a.

Referring for a moment to FIG. 3, opening 42 is formed by body section 43. Referring back to FIGS. 1 and 2, secondary flow is directed through chamber 38, as shown by the arrows, from entry port 40 to an exit port 42a where it continues to channel 24.

Referring to FIG. 2, exit port 42a associated with opening 42 has a first cross-sectional area 44 that is defined by a porous, gas-permeable, waste-blocking member 46 that extends into chamber 38. Referring to FIGS. 2 and 3, the ends of member 46 define the exit port by being fixed in opening 42 using a suitable material 50 such as a polymeric material. Preferably, member 46 takes the form of hydrophobic, microporous filter media that extends substantially across the chamber. Member 46 may also be of a tubular shape. Suitable filter media for member 46 is sold under the trademark Dynafibre by Microgon, Inc.

A key requirement of such filter media is that its liquid- or waste-intrusion pressure be sufficiently high so that there is no chance of liquid/waste passing through it during a measurement cycle. The Dynafibre material is suitable because its water-intrusion pressure is approximately 30-p.s.i. Because the pressure in chamber 38 never exceeds approximately 5–10 p.s.i. due to conventional capnometer design parameters, there appears to be no chance that waste will pass through member 46 if the Dynafibre material is used.

Another advantage of the Dynafibre material is that it will not wet below approximately 90% of its water-intrusion pressure, i.e. 25-p.s.i. Such non-wettability is important because, as will be further described, the pores of member 46 that are above the level of waste in trap 23 must not wet if the trap is momentarily tilted and waste splashes upon them. If such pores did wet, then they would become blocked, thus losing their gas permeability. Non-wetting occurs throughout operation of the capnometer in FIG. 1 because the pressure never rises to 25-p.s.i.

Figure 3A:
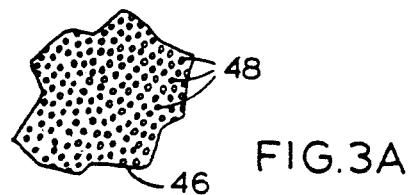
FIG. 3A is a fragmentary view of the waste-blocking member of the apparatus in FIG. 3.

Also, referring to FIG. 3A, a fragmentary portion of member 46 is shown with pores 48. The sum of the areas of all pores of member 46 equals a total-pore area exceeding first cross-sectional area 44. The importance of this relationship will be described, but for now it is enough to say that such relationship helps apparatus 10 promote waste-free primary flow independent of the orientation of body 36.

Referring for a moment to FIG. 4, a second embodiment of the invention is shown with plural members 146a, 146b, 146c positioned in the chamber (undepicted) to provide additional filtering capability. The ends of the plural members are fixed in the opening formed by body section 143 using a suitable material 150. Also, members may be positioned in any orientation within the chamber. For example the members may be formed with loops that are positioned together like the loops of a whisk used by cooks to prepare sauces.

Referring back to FIG. 1, operatively connected between ports 40 and 42a is means 52 for monitoring the differential pressure therebetween. Means 52, also referred to herein as differential pressure transducer, must be connected to either side of the chamber 38, but the exact position is not critical. Preferably, differential pressure transducer 52 is constructed to monitor continuously the difference in pressure between ports 40 and 42a.

A suitable differential pressure transducer may be obtained from any of the following companies: ICSensors, MICROSWITCH, Motorola, or SenSym.

Differential pressure transducer 52 is also operable to send signals representative of such trap-pressure differential to conventional control circuitry 54 of the capnometer. Such circuitry can be designed in known ways to recognize when a threshold signal from transducer 52 represents that trap 23 is approximately 90–95% full. Responding to such threshold signal from transducer 52, control circuitry 54 can also be designed in known ways to send a control signal to a conventional sound emitting device (undepicted) or a conventional display means (undepicted) associated with the capnometer.

The basis for determining the volume of waste in the trap using signal data received from transducer 52 will now be explained. Applicant recognized that in a given channel, pressure (P) is proportional to flow resistance R. The relationship can be expressed mathematically as:

$$P = GF \times R$$

where:
P = pressure (inches $H_2O$);
GF = gas flow in ml/min.; and
R = resistance in inches $H_2O$/ml/min.

Applying the above equation to conditions in body 36, the pressure therein will vary in proportion to flow resistance. Flow resistance will vary depending upon the level of waste in the chamber. This is because flow resistance in body 36 is supplied by member 46 and waste in the body. As will be understood, member 46 can be thought of as a variable resistor in contrast to fixed-type flow resistors like resistors 30a, 30b.

The following is a description of how the volume of waste in body 36 may be determined using transducer 52 and conventional control circuitry of the capnometer. When chamber 38 is empty, flow resistance through body 36 is caused only by the non-porous portions of member 46. Such a condition could be measured, using transducer 52. The signal sent by transducer 52 to control circuitry 54 could be understood by the circuitry, using known calibration techniques, as the 0%-resistance condition. When chamber 38 is filled to a threshold level, e.g. 90–95% full, flow resistance will increase because waste will block more gas-permeable pores of member 46. Again, following known calibration techniques, control circuitry 54 could be designed to trigger an audible/visible alarm device based upon receiving a signal from transducer 52 representative of this condition, referred to herein as the threshold condition.

As chamber 38 fills with waste, applicant has observed that there will be a two-phase rise in flow resistance in body 36. The first phase, which occurs when the chamber goes from 0% to about 80% full, is characterized by a relatively gradual rise in flow resistance. The second phase occurs above about the 80%-full condition, and is characterized by a relatively sharp rise in flow resistance.

The following is an example of such a two-phase rise in flow resistance. Four loops of member 46 were positioned in opening 42 of body 36 like the single loop shown in FIG. 2. 45-micron pore size Dynafibre tubing was used with each loop being approximately 2.5-inches long and each having an inside diameter of 0.015-inches. The chamber had a volume of approximately 3.5–4-ml. When the chamber was empty, the differential pressure across the trap was approximately 1-inch H₂O. While the chamber filled with waste to approximately 80%, there was relatively little change in trap-differential pressure. However, above the 80%-waste-level there was a relatively sharp change in differential pressure. At approximately the 95%-waste-level, the differential pressure rose to about 3-inches H₂O.

Applicant determined that the two-phase rise in flow resistance was caused by a variation in the relationship between the unblocked total-pore area of member 46 and the cross-sectional area of exit port 42a. That is, below about the 80%-waste-level, the unblocked total-pore area exceeded the cross-sectional area of the exit port. Above about the 80%-waste-level, the unblocked total-pore area became less than the cross-sectional area of the exit port.

Put another way, applicant found that if the unblocked total-pore area exceeded the cross-sectional area of the exit port, then the absolute value of the slope of the differential-trap pressure with respect to differential-waste-volume was relatively low. If the unblocked total-pore area became less than the cross-sectional area of the exit port, then the absolute value of the slope of the differential-trap pressure with respect to differential-waste-volume exhibited a relatively sharp increase that was reliably measurable using transducer 52.

OPERATION

Referring to FIG. 1, a measurement cycle is begun in the usual way by inserting the intake (undepicted) of tube 12 in the patient's airway. Pump 22 is activated using the usual control mechanism of the capnometer. A negative pressure will exist in both gas-sensing channel 16 and secondary channel 24. The patient's breath will be conducted from the intake to tube 12 which will carry it to gas/liquid separator 14. Approximately 92.5% by volume of the gas component will be directed to channel 16 and the remaining 7.5% of the gas component, as well as the entire waste component will be directed to chamber 38 via entry port 40. Referring to FIG. 2, during a measurement cycle chamber 38 will begin to fill with waste depicted generally at 56.

Figure 5:
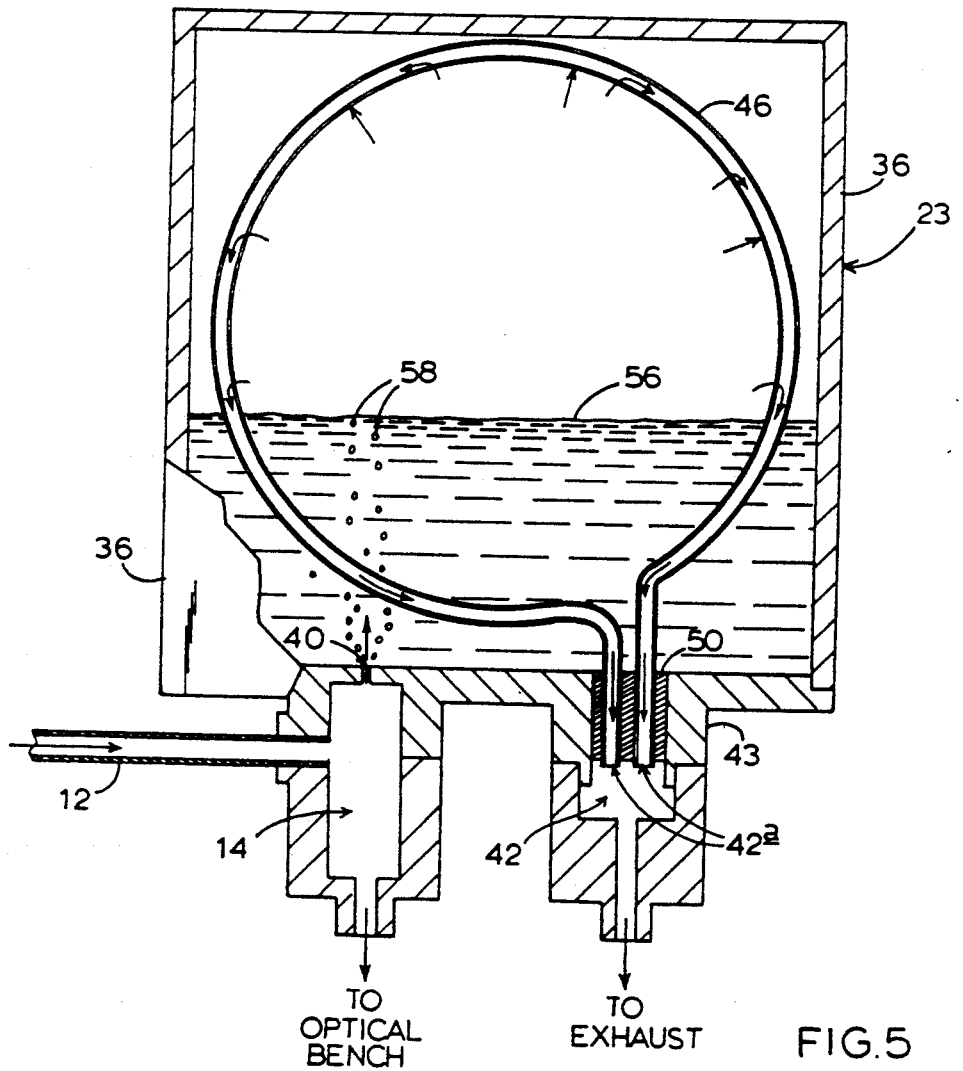
FIG. 5 is a sectional view like FIG. 2 except that the invention and conventional gas/liquid separator are inverted and viewed from the side opposite that shown in FIG. 2.

Referring to FIG. 5, if trap 23 is inverted during measurement then waste-free primary flow will be promoted and secondary flow will be preserved in chamber 38 because member 46 extends into the chamber above the level of waste where it can contact a gas-containing portion of the same. Another reason that primary flow is promoted and secondary flow is preserved is because the total-pore area of member 46 is greater than first cross-sectional area 44.

As shown in FIG. 5, the waste and gas components of the patient's breath will be drawn into chamber 38 via entry port 40. Gas bubbles 58 will rise from port 40 through waste 56 and eventually to the volume of gas in the chamber. Referring to FIGS. 3 and 5, secondary flow will be preserved, and waste-free primary flow will be promoted, because the non-wetting portion of member 46 that is not blocked by waste will be gas-permeable as shown by the arrows. Thus, gas will be drawn inside member 46 and out of the chamber via exit port 42a.

The non-wettability of member 46 is important because it allows portions of the member that were previously blocked by waste to regain their gas-permeability. For example, referring to the bottom of chamber 38 shown near the bottom of FIG. 2, a portion of member 46 is blocked by waste 56. In other words, the blocked portion is not gas permeable when the trap is oriented as in FIG. 2. However, referring to the bottom of chamber 38 shown near the top of FIG. 5, the previously blocked portion of member 46 is now gas-permeable because waste 56 flowed to the top of the inverted chamber and because member 46 is non-wetting. That is, once waste 56 flowed from the previously blocked portion, the non-wettability of the member 46 allowed the portion to regain its gas-permeability.

Referring to FIG. 1, differential pressure transducer 52 will continuously monitor the pressure difference across trap 23 and send signal data to control circuitry 54 which will be programmed in known ways for alerting the user if the threshold condition exists in chamber 38. Presently, it is intended that the control circuitry will activate known alarm devices to alert the user when the chamber is about 90–95% filled. The circuitry could also be programmed automatically to shut off pump 22 on the occurrence of the threshold condition. Also, in addition to automatic shut-off of pump 22, the circuitry could be programmed to activate an alarm at a preselected time before occurrence of the threshold condition, and before automatic shut-off of the pump.

It will now be clear to those skilled in the art that apparatus 10 will promote waste-free primary flow and preserve secondary flow in a patient monitoring device during a measurement cycle. In addition, apparatus 10 will preserve secondary flow independent of the orientation of the trap. Apparatus 10 also accomplishes the object of providing means for monitoring the volume of waste in trap 23 during a measurement cycle as a way of promoting waste-free primary flow by providing signals to known circuitry that is designed to let the user know if the threshold condition exists.

While the present invention has been shown and described with reference to the foregoing preferred embodiment, it will be apparent to those skilled in the art that other changes in form and detail may be made therein without departing from the spirit and scope of the invention as defined in the appended claims.

What is claimed is:

1. Apparatus for promoting waste-free primary flow in a patient monitoring device during a measurement cycle, such device including a gas-sensing channel for conducting primary flow and a secondary channel for conducting secondary flow, with each such channel having a negative pressure existing therein, said apparatus comprising:

a waste trap with a body defining a waste chamber, said body including an entry port for communication with the gas-sensing channel and an exit port for communication with the secondary channel, and structure for directing said secondary flow through said body from the entry port to the exit port where it continues through the secondary channel; and said exit port comprising a porous, gas-permeable, waste-blocking member that extends into the chamber, for providing waste-free primary flow independent of the orientation of said body.

2. The apparatus of claim 1 wherein said exit port has a first cross-sectional area, and said member has a total-pore area exceeding said first cross-sectional area.

3. The apparatus of claim 2 wherein said waste-blocking member extends from said exit port substantially across the chamber.

* * * * *